(12) United States Patent　　(10) Patent No.: US 11,744,411 B2
McKinley, Jr. et al.　　(45) Date of Patent: Sep. 5, 2023

(54) HAND SANITIZING STATION

(71) Applicant: Clean Hand Station USA, LLC, Houston, TX (US)

(72) Inventors: Robert H. McKinley, Jr., Houston, TX (US); William Davis Massey, Houston, TX (US)

(73) Assignee: Clean Hand Station USA, LLC, Houston, TX (US)

( * ) Notice: Subject to any disclaimer, the term of this patent is extended or adjusted under 35 U.S.C. 154(b) by 24 days.

(21) Appl. No.: 17/327,522

(22) Filed: May 21, 2021

(65) Prior Publication Data

US 2021/0361124 A1 Nov. 25, 2021

Related U.S. Application Data

(60) Provisional application No. 63/027,998, filed on May 21, 2020.

(51) Int. Cl.
*A47K 5/12* (2006.01)
*A61L 2/00* (2006.01)

(52) U.S. Cl.
CPC .......... *A47K 5/1202* (2013.01); *A61L 2/0088* (2013.01); *A47K 2005/1218* (2013.01);
(Continued)

(58) Field of Classification Search
CPC .......... A47K 5/1202; A47K 2005/1218; A61L 2/0088; A61L 2202/15; A61L 2202/17; A61L 2202/18
See application file for complete search history.

(56) References Cited

U.S. PATENT DOCUMENTS 1,794,484 A  *  3/1931  Seidel ................ F16K 31/62
　　　　　　　　　　　　　　　　　　　222/375
1,939,981 A  *  12/1933  Hillyard ............. A47K 5/1214
　　　　　　　　　　　　　　　　　　　222/509
(Continued)

FOREIGN PATENT DOCUMENTS

| KR | 20090032503 A | 4/2009 |
| KR | 20110004385 U | 5/2011 |
| KR | 101789941 B1 | 11/2017 |

OTHER PUBLICATIONS

International Patent Application No. PCT/US2021/033751 International Search Report and Written Opinion dated Sep. 9, 2021 (9 pages).

*Primary Examiner* — Vishal Pancholi
(74) *Attorney, Agent, or Firm* — Conley Rose, P.C.

(57) ABSTRACT

A hand sanitizing station includes a conduit in fluid communication with a source of sanitizer, the conduit having a fluid outlet. In addition, the hand sanitizing station includes a valve coupled to the conduit and configured to control the volume of sanitizer that exits the fluid outlet, the valve having a control arm. Further, the hand sanitizing station includes a pedal, and a cable connected between the pedal and the control arm of the valve and configured to move the control arm when the pedal is depressed and open the valve a predetermined amount. Movement of the pedal from a first position to a second position causes sanitizer to flow by gravity from the conduit and out of the fluid outlet, and movement of the pedal from the second position back to the first position closes the valve.

16 Claims, 8 Drawing Sheets

(52) U.S. Cl.
CPC ....... *A47K 2210/00* (2013.01); *A61L 2202/15* (2013.01); *A61L 2202/17* (2013.01); *A61L 2202/18* (2013.01)

(56) References Cited

U.S. PATENT DOCUMENTS

| | | | | |
|---|---|---|---|---|
| 1,949,315 | A | * | 2/1934 | Levernier ............ A47K 5/1205 222/465.1 |
| 2,494,147 | A | * | 1/1950 | Trelease ................ A01K 39/06 222/400.5 |
| 3,090,528 | A | * | 5/1963 | Ellis ........................ A47K 5/06 222/212 |
| 3,197,081 | A | | 7/1965 | Midworth |
| 5,897,031 | A | * | 4/1999 | Wirt ................... B05B 11/3097 222/375 |
| 5,996,851 | A | * | 12/1999 | Dolan ................ A47K 5/1209 222/181.3 |
| 2007/0213877 | A1 | * | 9/2007 | Hart ........................ G07C 9/22 700/282 |
| 2011/0132931 | A1 | | 6/2011 | Wright |
| 2017/0036250 | A1 | | 2/2017 | Stopponi |

\* cited by examiner

HAND SANITIZING STATION

CROSS-REFERENCE TO RELATED APPLICATIONS

This application claims benefit of U.S. provisional patent application Ser. No. 63/027,998 filed May 21, 2020, and entitled "Hand Sanitizing Station," which is hereby incorporated herein by reference in its entirety.

BACKGROUND

Frequent washing of hands is a strong deterrent to the spread of bacteria and viruses. Sanitizer applied to hands is also a deterrent. However, especially at large crowd events, such as sporting events, concerts, church services, and even in bars and restaurants, visitors and patrons may not wash and sanitize their hands as frequently as would be optimum to prevent the spread of disease.

The recent spread of the novel coronavirus has heightened the awareness of the need for these hygienic precautions. Further, with restaurants, bars, schools, retail stores and events reopening (following quarantines and stay at home orders being rescinded) there exists a very pressing need for a means by which large numbers of patrons can sanitize their hands in such establishments (e.g., such as when the patrons enter the establishment or venue).

BRIEF SUMMARY

Some embodiments disclosed herein are directed to a hand sanitizing station. In some embodiments, the hand sanitizing station includes a conduit in fluid communication with a source of sanitizer, the conduit having a fluid outlet. In addition, the hand sanitizing station includes a valve coupled to the conduit and configured to control the volume of sanitizer that exits the fluid outlet, the valve having a control arm. Further, the hand sanitizing station includes a pedal, and a cable connected between the pedal and the control arm of the valve and configured to move the control arm when the pedal is depressed and open the valve a predetermined amount. Movement of the pedal from a first position to a second position causes sanitizer to flow by gravity from the conduit and out of the fluid outlet, and movement of the pedal from the second position back to the first position closes the valve.

Some embodiments disclosed herein are directed to a method of sanitizing hands. In some embodiments, the method includes (a) depressing a pedal on a hand sanitizing station. In addition, the method includes (b) actuating a valve positioned within a housing of the hand sanitizing station as a result of (a). Further, the method includes (c) flowing sanitizer from a supply tank positioned within the hand sanitizing station through a nozzle as a result of (b) under the force of gravity.

Embodiments described herein comprise a combination of features and characteristics intended to address various shortcomings associated with certain prior devices, systems, and methods. The foregoing has outlined rather broadly the features and technical characteristics of the disclosed embodiments in order that the detailed description that follows may be better understood. The various characteristics and features described above, as well as others, will be readily apparent to those skilled in the art upon reading the following detailed description, and by referring to the accompanying drawings. It should be appreciated that the conception and the specific embodiments disclosed may be readily utilized as a basis for modifying or designing other structures for carrying out the same purposes as the disclosed embodiments. It should also be realized that such equivalent constructions do not depart from the spirit and scope of the principles disclosed herein.

BRIEF DESCRIPTION OF THE DRAWINGS

For a detailed description of various exemplary embodiments, reference will now be made to the accompanying drawings in which.

DETAILED DESCRIPTION

The following discussion is directed to various exemplary embodiments. However, one of ordinary skill in the art will understand that the examples disclosed herein have broad application, and that the discussion of any embodiment is meant only to be exemplary of that embodiment, and not intended to suggest that the scope of the disclosure, including the claims, is limited to that embodiment.

The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection of the two devices, or through an indirect connection that is established via other devices, components, nodes, and connections. In addition, as used herein, the terms "axial" and "axially" generally mean along or parallel to a given axis (e.g., central axis of a body or a port), while the terms "radial" and "radially" generally mean perpendicular to the given axis. For instance, an axial distance refers to a distance measured along or parallel to the axis, and a radial distance means a distance measured perpendicular to the axis. Further, when used herein (including in the claims), the words "about," "generally," "substantially," "approximately," and the like mean within a range of plus or minus 10%.

As previously described, there exists a need for a means by which large numbers of patrons can sanitize their hands in public establishments or venues (e.g., such as when the patrons enter the establishment or venue). Accordingly, embodiments disclosed herein include a self-contained hand sanitation station that operates without electricity or other sources of power and relies instead on the head pressure of the sanitizer that is retained in a reservoir. A measured amount of fluid sanitizer is metered out of the apparatus onto the patron's hands as controlled by a foot pedal that the patron depresses. As explained in more detail below, in some embodiments the patron presses the foot pedal which causes a valve to open so that a predetermined and proper amount of sanitizer is deposited by gravity and head pressure on the patron's hands. The apparatus thus described is not dependent on electric power, hydraulic power or other power source and instead relies only on the patron depressing a foot pedal and on there being a head pressure of sanitizer to convey the sanitizer through the valve. The apparatus is simple and reliable and not dependent on motors or pumps which must be serviced and maintained regularly to ensure their operation and in turn, to ensure that sanitizer would be available. Thus, the hand sanitation station 10 may be described as "pumpless."

Figure 1:
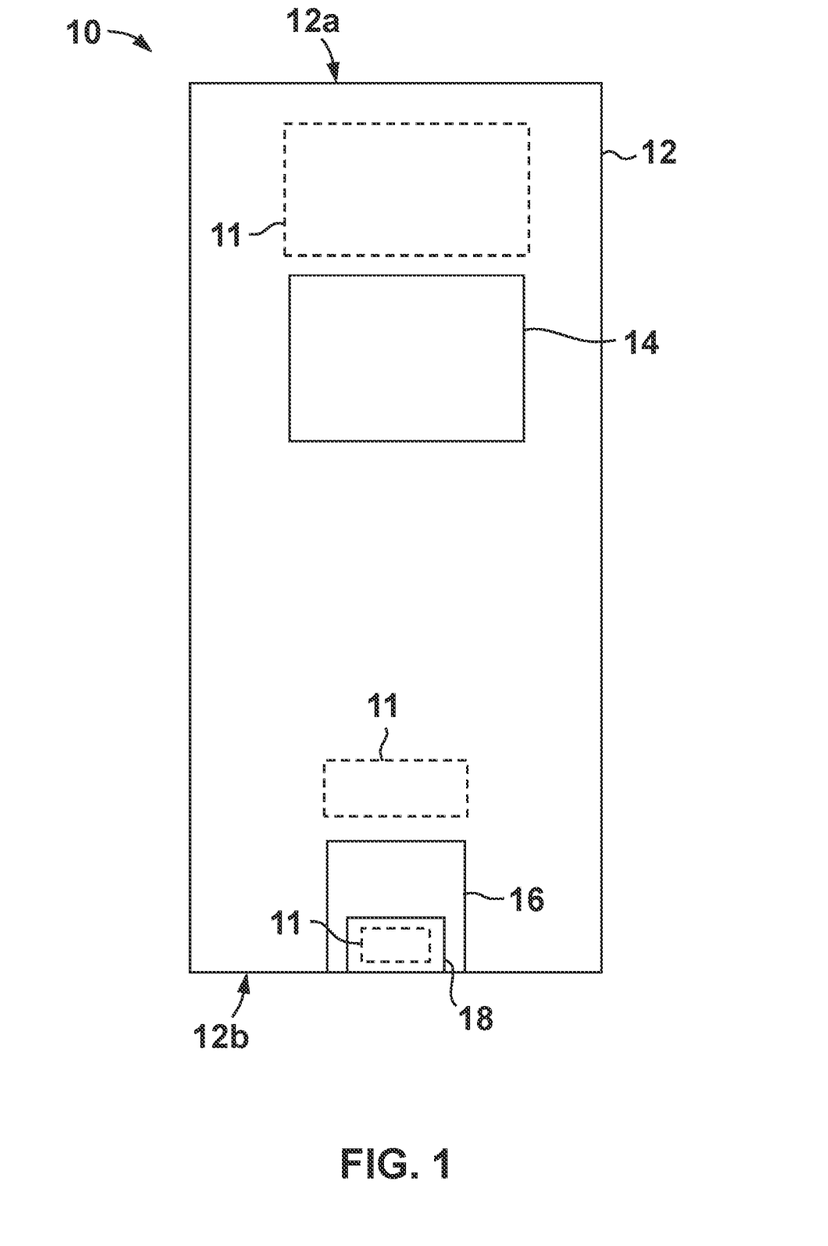
FIG. 1 is a front view of a hand sanitizing station according to some embodiments.

Referring now to FIG. 1, a hand sanitizing station 10 according to some embodiments is shown. Hand sanitizing station 10 includes an outer housing 12 including a first or upper end 12a, and a second or lower end 12b opposite upper end 12a. Housing includes a first recess 14 in which a user may place their hands to contact a stream of hand sanitizer (or more simply "sanitizer"). As used herein the terms "hand sanitizer" "sanitizer" and the like refer to any fluid (e.g., liquid, gel, etc.) that is configured to kill or inactivate microbes (e.g., viruses, bacteria), and may include, in some examples, isopropyl alcohol (but other ingredients are contemplated). In addition, outer housing 12 includes a second recess 16 that may provide access to a pedal 18. During operations, a user may engage the pedal 18 with their foot so as to induce a flow of hand sanitizer into the first recess 14. The second aperture 16 may be positioned at or near the lower end 12b, and the first recess 14 may be vertically spaced above the second recess 16 (e.g., such that the first recess 14 is more proximate the upper end 12a than the second recess 16). The first recess 14 and the second recess 16 may be placed along the same side (e.g., a front side) of the outer housing 12.

Figure 2:
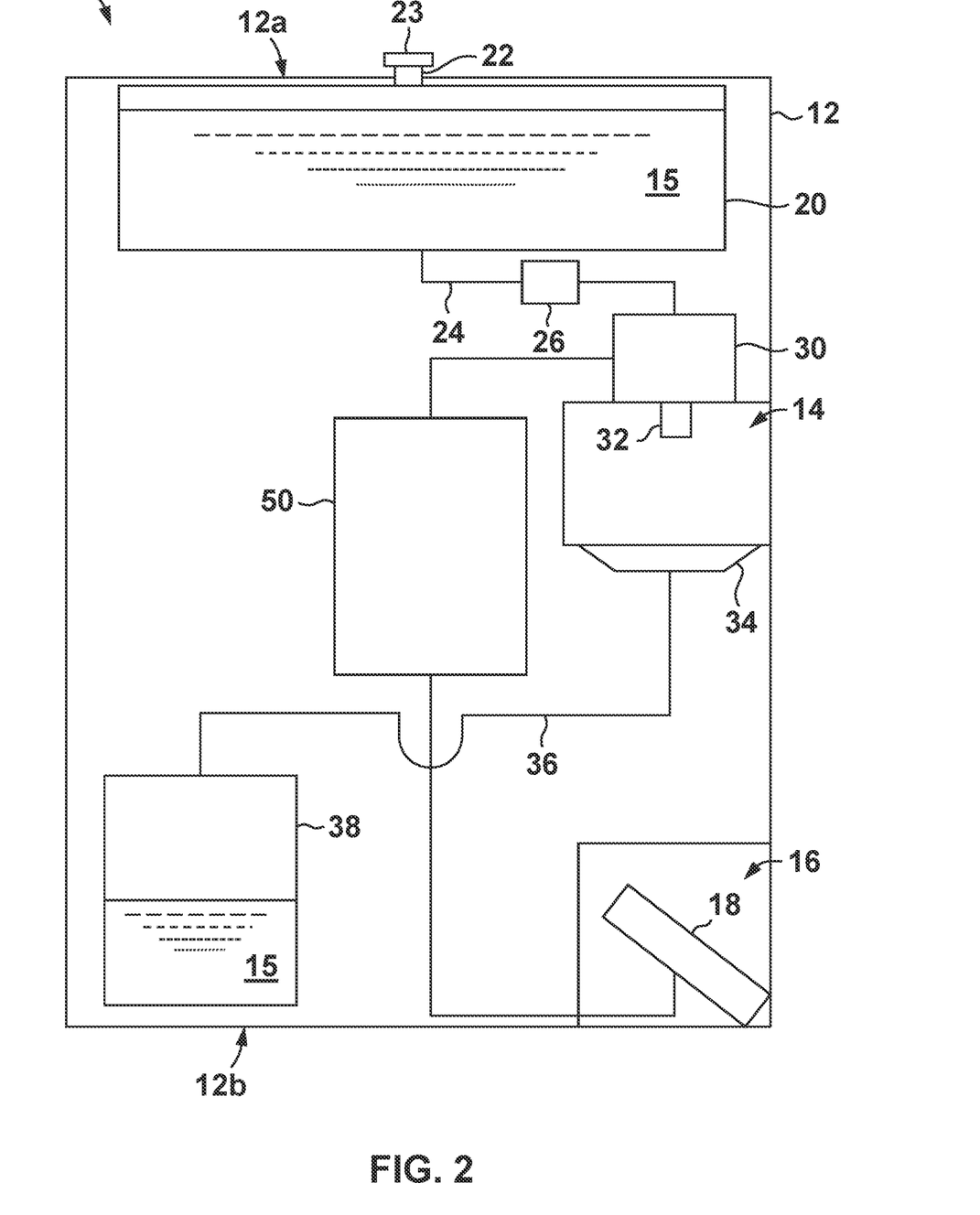
FIG. 2 is a schematic diagram of the hand sanitizing station of FIG. 1 according to some embodiments.

Referring now to FIG. 2, a schematic diagram of hand sanitizing station 10 according to some embodiments is shown. In some embodiments, hand sanitizing station 10 comprises a supply tank or reservoir 20 that positioned within housing 12, at or proximate upper end 12a. Supply tank 20 includes a opening 22 that is extends upward through the upper end 12a, so that during operations, hand sanitizer 15 may be filled into supply tank 20 via opening 22. As shown in FIG. 2, the opening 22 may be closed by a cap 23 (e.g., snap fit cap, threaded cap). In some embodiments, supply tank 20 may be removed from housing 12 for servicing and/or replacement.

In addition, hand sanitizing station 10 includes a flow control valve assembly 30 that includes a fluid outlet or nozzle 32 communicating with first recess 14. Flow control valve assembly 30 may be fluidly coupled to the supply tank 20 via a supply line 24 which may comprise a hose, pipe, or other suitable conduit. As a result, during operations, hand sanitizer 15 that is held within supply tank 20 may flow, via head pressure alone, from supply tank 20, through supply line 24 and into flow control valve assembly 30. Thereafter, actuation of the flow control valve assembly 30 (described in more detail below) may allow hand sanitizer 15 to flow out of nozzle 32 and into first recess 14 whereby it may contact a user's hands (not shown).

A flow restrictor valve 26 may be positioned along supply line 24, between supply tank 20 and flow control valve assembly 30. Flow restrictor valve 26 may be actuated between a fully open position, a fully closed position, and a plurality of positions between the fully open and fully closed positions to control a flow rate of hand sanitizer 15 between the supply tank 20 and flow control valve assembly 30. In particular, flow restrictor valve 26 may be actuated to a suitable position (e.g., between the fully open and fully closed positions) to result in a desired, proportional flow rate of hand sanitizer 15 along supply line 24 to flow control valve assembly 30. Without being limited to this or any other theory, as the viscosity of the hand sanitizer 15 increases, the flow restrictor valve 26 may be actuated toward the fully opened position to achieve a desired flow rate for ensuring a reliable supply of hand sanitizer 15 to the flow control valve assembly 30. Conversely, as the viscosity of the hand sanitizer decreases, the flow restrictor valve 26 may be actuated toward the fully closed position to achieve the desired flow rate for ensuring a reliable supply of hand sanitizer 15 to the flow control valve assembly 30.

A basin 34 may be formed or defined within first recess 14 that is to collect dispensed hand sanitizer 15 that is not used or captured by a user during operations. A drain line 36, which may also comprise a hose, pipe, or other suitable conduit, may communicate hand sanitizer 15 received into basin 34 to a waste tank or reservoir 38, again via head pressure. The waste reservoir 38 may be positioned within housing 12 at or proximate lower end 12b.

As may be appreciated from FIG. 2, the first recess 14, flow control valve assembly 30 and nozzle 32 may be positioned vertically between supply tank 20 and waste tank 38, with supply tank 20 being positioned vertically higher than waste tank 38. As a result, during operations, the hand sanitizer 15 may be flowed from supply tank 20, through nozzle 32, and into waste tank 38 under the force of gravity. Thus, flow of hand sanitizer 15 within hand sanitizing station 10 may be driven by head pressure of the hand sanitizer 15 such that hand sanitizing station 10 is free of pumps or power sources.

Generally speaking, the flow control valve assembly 30 may be actuated to selectively flow hand sanitizer 15 out of nozzle 32 by engagement of pedal 18 (e.g., via a user's foot). In particular, a mechanical coupling assembly 50 is coupled between pedal 18 and flow control valve assembly 30 that is configured to transfer forces therebetween. Thus, during operations, a user may engage with and depress pedal 18 (e.g., with a foot or other appendage or device) and the mechanical coupling assembly 50 may convert the movement of pedal 18 into a force that is applied to flow control valve assembly 30 so as to actuate valve assembly 30 and induce a flow of hand sanitizer 15 out of nozzle 32 as previously described. Further details of embodiments of pedal 18, flow control valve assembly 30, and mechanical coupling assembly 50 are provided below. Instructional markings 11, which may comprise text, images, graphics, etc. may be placed on the outer housing 12 (e.g., such as adjacent to, above, and/or below first recess 14 and/or second recess 16), and/or on pedal 18 for instructing a user how to operate the hand sanitizing station 10 during operations.

Figure 3:
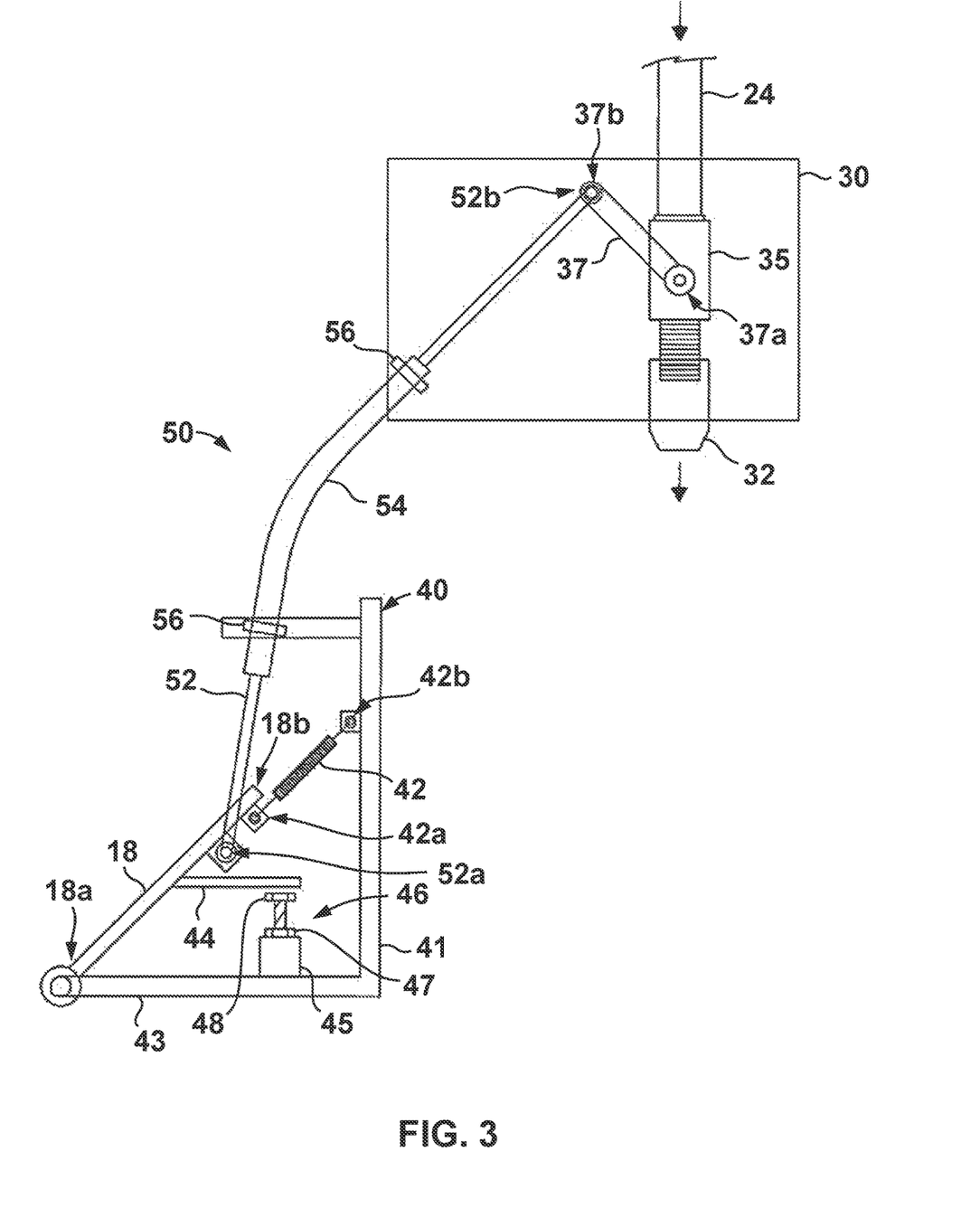
FIG. 3 is a schematic view of a flow control valve assembly 30, mechanical coupling assembly, and pedal of the hand sanitizing station of FIG. 1 according to some embodiments.

Referring now to FIG. 3, a partially schematic view of the pedal 18, mechanical coupling assembly 50 and flow control valve assembly 30 of hand sanitizing station 10 (FIGS. 1 and 2) is shown. However, it should be appreciated that other components of the hand sanitizing station 10 (e.g., other than pedal 18, mechanical coupling assembly 50 and flow control valve assembly 30) are not shown in FIG. 3 so as to simplify the drawing.

In some embodiments, pedal 18 may be pivotably coupled to a support frame 40 that may be positioned within outer housing 12 of hand sanitizing station 10 (FIG. 2). In some embodiments, the support frame 40 may be L-shaped in side view and include a vertical portion 41 and a lateral portion or base 43 extending perpendicularly from vertical portion 41. Pedal 18 is an elongate member having a first end 18a and a second end 18b opposite the first end 18a. The first end 18a may be pivotably coupled to lateral portion 43 of support frame 40 via a pinned connection (e.g., a bronze bushing and pivot pin assembly). Thus, during operations, the pedal 18 may be pivoted about first end 18a relative to support frame 40.

A biasing member 42 is coupled to pedal 18. In some embodiments, the biasing member 42 is coupled to pedal 18 proximate second end 18b (e.g., more proximate second end 18b than first end 18a). The biasing member 42 may comprise a coiled spring having a first end 42a coupled to pedal 18 and a second end 42b opposite first end 42a that is coupled to vertical portion 41 of support frame 40. In some embodiments, the ends 42a, 42b may be pivotably coupled to pedal 18 and vertical portion 41 of frame 40 via a suitable connection (e.g., pinned connection). During operations, the biasing member 42 may bias ends 42a, 42b toward one another so that second end 18b of pedal 18 is rotationally biased away upward and away from lateral portion 43 of support frame 40 about the pinned connection at first end 18a of pedal 18. According, when a user depresses pedal 18 (e.g., with a foot), the second end 18b of pedal 18 may rotate against the bias provided by biasing member 42 about first end 18a, in a downward direction, toward lateral portion 43 of support frame 40 (e.g., in a clockwise direction in the view of FIG. 3). When the user disengages pedal 18, the biasing member 42 may then drive rotation of the second end 18b of pedal 18 about first end 18a upward and away from lateral portion 43 of support frame 40 (e.g., in a counter clockwise direction in the view of FIG. 3).

A pedal stop assembly 46 is coupled to support frame 40 that includes a stop member 48 that is to engage with pedal 18 (or an extension thereof or component coupled thereto) to define a maximum downward rotation of pedal 18 relative to support frame 40 during operations. In particular, in some embodiments, the stop member 48 comprises a threaded bolt that is threadably engaged within a receptacle 45 coupled to lateral portion 43 of support frame 40. Threadably advancing or retracting the stop member 48 into or out of, respectively, the receptacle 45 may adjust a height of stop member 48 relative to lateral portion 43 of support frame 40 and therefore the maximum downward rotation of pedal 18 about first end 18a during operations. A lock nut 47 may be threadably engaged with stop member 48 that may be threadably tightened against the receptacle 45 to lock a position of stop member 48 relative to receptacle 45 during operations.

Referring still to FIG. 3, in some embodiments, stop member 48 may engage with pedal 18 or an extension thereof or a component coupled thereto. In particular, in some embodiments, stop member 48 may engage with an extension 44 coupled to pedal 18 (e.g., coupled to and extending from pedal 18 at a point spaced from the ends 18a, 18b). Thus, during operations, a user may depress pedal 18 by rotating second end 18b about first end 18a downward and toward lateral portion 43 of support frame 40 until extension 44 engages or abuts with stop member 48.

Figure 4:
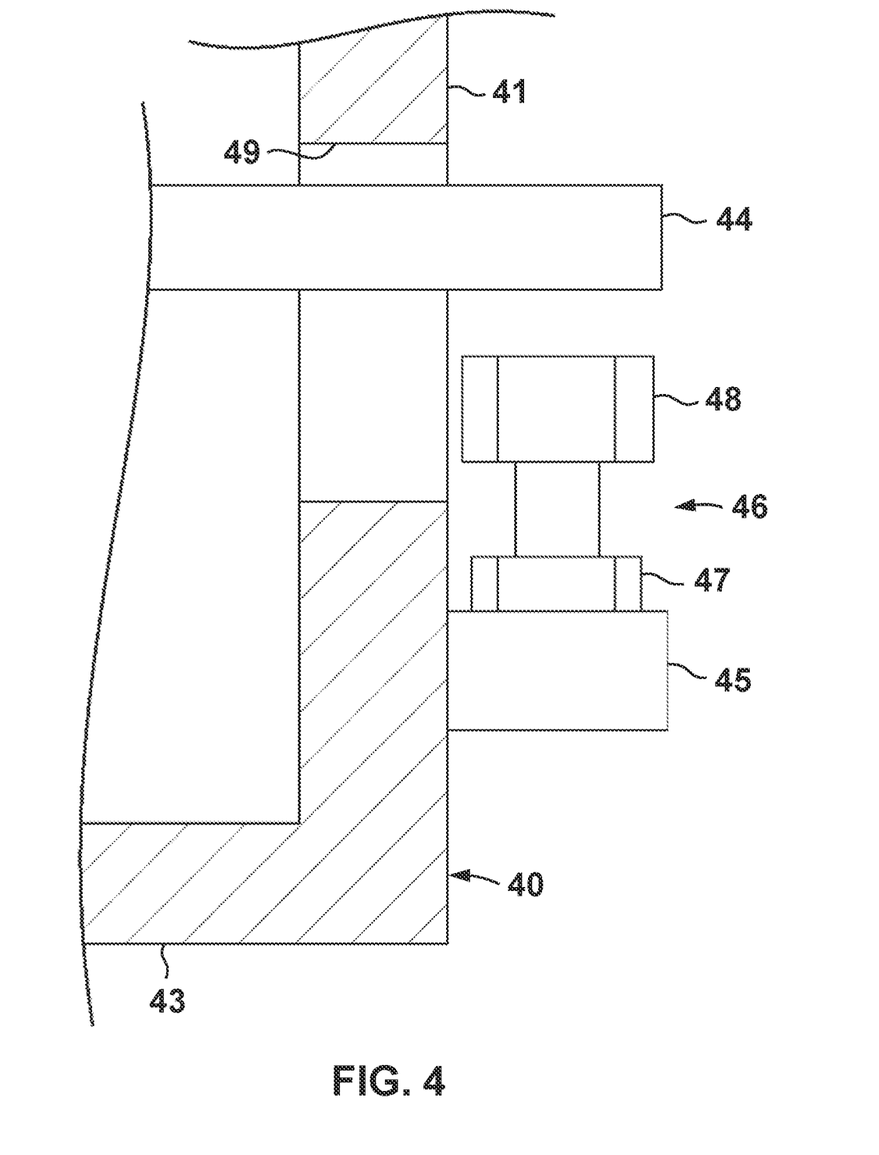
FIG. 4 is an enlarged, side cross-sectional view of a support housing and pedal stop assembly of the hand sanitizing station of FIG. 1 according to some embodiments.

Referring briefly to FIG. 4, in some embodiments, pedal stop assembly 46 may be positioned outside of support frame 40 and specifically on or along a side of vertical portion 41 that is opposite lateral portion 43 and pedal 18. In particular, the receptacle 45 may be secured to vertical portion 41 (e.g., via welding, bracket, etc.), and extension 44 coupled to pedal 18 (FIG. 3) may extend through an aperture 49 in vertical portion 41 to engage with stop member 48 as pedal 18 (FIG. 3) rotates about first end 18a as previously described. Without being limited to this or any other theory, placement of the pedal stop assembly 46 in the manner shown in FIG. 4 and described above may allow the pedal stop assembly 46 to be accessible without removing or accessing the inside of support housing 44 (e.g., the portion between pedal 18 and vertical portion 41 as shown in FIG. 3), such that the maximum downward rotation of pedal 18 may be more easily adjusted during operations.

Referring again to FIG. 3, flow control valve assembly 30 includes a valve 35 coupled between supply line 24 and nozzle 32. The valve 35 may comprise any suitable valve type or design for selectively allowing or restricting a flow of fluid (e.g., hand sanitizer 15) through supply line 24 to nozzle 32 during operations. For instance, in some embodiments, the valve 35 may comprise a ball valve (e.g., stainless steel ball valve such as a #6 Ball Shutoff Valve available from Enderle). In some embodiments, the valve 35 may comprise a barrel valve that defines or includes a chamber (not shown) therein that is to receive hand sanitizer 15 from supply line 24. Actuation of valve 35 may communicate the hand sanitizer 15 held within the chamber to then flow to and through nozzle 32. Thus, in some embodiments, the valve 35 may meter out a selected or desired dose or volume of hand sanitizer 15 with each actuation of valve 35 (e.g., via pedal 18 as described herein).

A control arm or actuator 37 is coupled to the valve elements within valve 35 such that rotation of actuator 37 may cause actuation of the valve elements (e.g., a ball, piston, rod, needle, gate, etc.—not shown) within valve 35 so as to selectively allow hand sanitizer 15 to flow through valve 35 and into nozzle 32. Actuator 37 may comprise a first end 37a coupled to valve 35 and a second end 37b extending away from first end 37a. In some embodiments, pivoting of the second end 37b relative to the first end 37a may cause actuation of the valving elements (not shown) within valve 35 so as to allow hand sanitizer 15 to flow through valve 35 into nozzle 32. In some embodiments, the actuator 37 may be rotationally biased (e.g., via a biasing member coupled to and/or positioned within valve 35) such that second end 37b is rotationally biased relative to first end 37a and valve 35 is biased to a closed position (e.g., whereby hand sanitizer 15 is prevented or at least restricted from flowing out of valve 35 into nozzle 32). In some embodiments, the rotation of the actuator 37 (e.g., rotation of actuator 37 about first end 37a) may open or close the valve 35 a proportional amount, which may correspond with a proportional flow rate of hand sanitizer 15 out of nozzle 32 during operations.

Mechanical coupling assembly 50 may comprise any suitable device(s) or linkage(s) that are to mechanically couple the pedal 18 to the actuator 37 of valve 35. As will be described in more detail below, depression of the pedal 18 (e.g., so as to rotate second end 18b of pedal 18 about first 18a, downward toward the lateral portion 43 of support frame 40) is configured to rotate the second end 37b of actuator 37 relative to first end 37a via the mechanical coupling assembly 50. In some embodiments, mechanical coupling assembly 50 comprises a cable 52 having a first end 52a coupled to pedal 18, and a second end 52b coupled to second end 37b of actuator 37. The cable 52 may comprise a push pull airline linkage cable in some embodiments. The ends 52a, 52b may be pivotably coupled to pedal 18 and second end 37b of actuator 37, respectively, via suitable connections (e.g., pinned connections). In some embodiments, the cable 52 may comprise a stainless steel cable 52. In some embodiments, elongate rods may be engaged between ends 52a, 52b of cable 52 and pedal 18 and actuator 37, respectively. In some embodiments, the cable 52 may be approximately 3 to 4 feet long.

A protective sheath 54 is positioned about some or all of the cable 52, between ends 52a, 52b so as to guide movement of the cable 52 and to prevent contact between cable 52 and other components or surfaces within outer housing 12 of hand sanitizing station 10 (FIGS. 1 and 2). The protective sheath 54 may be engaged to both the support frame 40 and the flow control valve assembly 30 (or a housing or bracket coupled thereto) via a pair of pivoting cable restraints 56. As a result, during operations, the cable 52 may slide within and relative to sheath 54 during operations. Without being limited to this or any other theory, the pivoting cable restraints 56 may fix sheath 54 to support frame 40 and flow control valve assembly 30 while allowing some movement (e.g., such as rotation or pivoting about a longitudinal axis of the cable 52 and/or sheath 54) during operations.

Accordingly, during operations, a user may depress pedal 18 so as to second end 18b downward and toward lateral portion 43 of support frame 40 about first end 18a. As previously described the downward rotation of second end 18b of pedal 18 may continue until extension 44 engages with stop member 48 of pedal stop assembly 46. In addition, as second end 18b of pedal rotates downward, toward lateral portion 43 of support frame 40, the first end 52a of cable 50 is pulled (or tensioned) along with the pedal 18 and the cable 52 is slid within sheath 54 such that second end 52b is retracted toward sheath 54. The retraction of second end 52b of cable 54 within sheath 54 further places tension on second end 37b of actuator 37 such that actuator 37 is rotated about first end 37a to thereby actuate valve 35 and allow hand sanitizer 15 to flow through valve 35 and into (and through) nozzle 32 as previously described.

As previously described, in some embodiments, the rotation of actuator 37 may open or close the valve 35 a proportional amount. As a result, a user may determine (e.g., within limits) a flow rate of hand sanitizer 15 emitted from nozzle 32 based on a proportional depression of pedal 18 during operations (e.g., a smaller depression of pedal 18 may result in a reduced rotation of actuator 37 and thus a lower flow rate of hand sanitizer 15 from nozzle 32). Accordingly, adjustment of the height of stop member 48 above receptacle 45 of pedal stop assembly 46 may not only adjust a maximum depression of the pedal 18 but may also adjust a corresponding maximum flow rate of hand sanitizer 15 from nozzle 32. Without being limited to this or any other theory, adjustments of the height of stop member 48 above receptacle 45 may be made to achieve a desired maximum flow rate of the hand sanitizer 15, based on a viscosity of the particular hand sanitizer being used. For instance, a thinner less viscous hand sanitizer 15 may achieve the desired flow rate with a smaller proportional opening of valve 35, and a thicker more viscous hand sanitizer 15 may achieve the desired flow rate with a larger proportional opening of valve 35.

After the pedal 18 is depressed and hand sanitizer 15 is emitted from nozzle 32, the user may disengage or release pedal 18 so that second end 18b may rotate upward and away from lateral portion 43 of support frame 40 via the biasing member 42 as previously described. The upward rotation of second end 18b of pedal 18 may also push the first end 52a of cable 52 into sheath 54 so that second end 52b of cable 52 is in turn extended outward from sheath 54. As second end 52b of cable 52 extends outward from sheath 52, the second end 37b of actuator 37 is also rotated about first end 37a so as to once again actuate valve 35 to a closed position to prevent (or at least restrict) the flow of hand sanitizer 15 into nozzle 32 as previously described. In addition, as previously described, the actuator 37 may also be rotationally biased to close the valve 35 so that second end 52a may also be pulled by outward from sheath 54 via actuator 37 when a user releases or disengages pedal 18.

In some embodiments, depression of the pedal 18 may be accomplished with the user's foot. As a result, during operations, a user may utilize the hand sanitizing station 10 to dispense hand sanitizer 15 without touching any of the surfaces of the hand sanitizing station 10 with their hand, which may further prevent the spread of viruses and bacteria.

Figure 5:
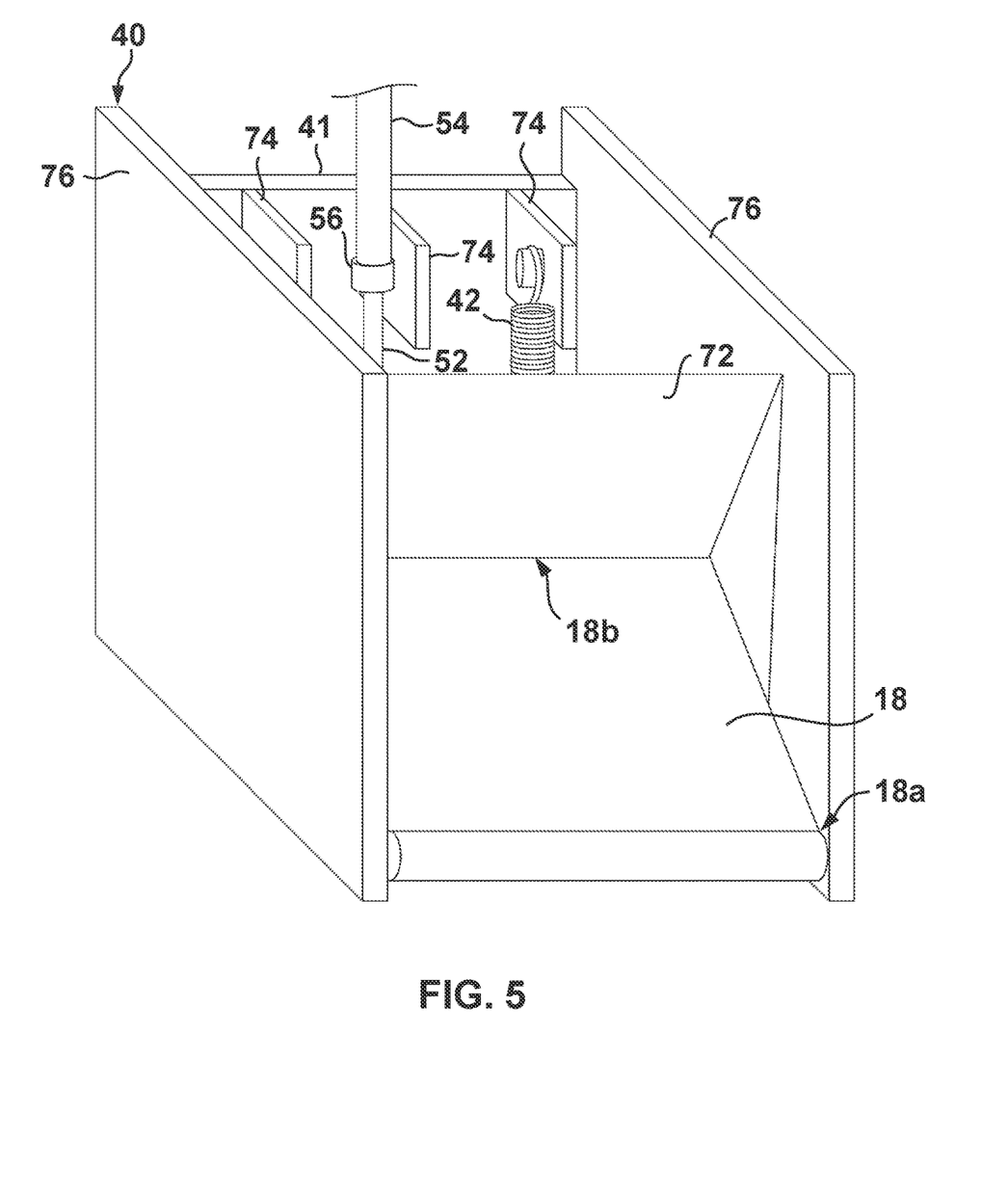
FIGS. 5 and 6 are perspective and front views of a support housing and pedal of the hand sanitizing station of FIG. 1 according to some embodiments.
Figure 6:
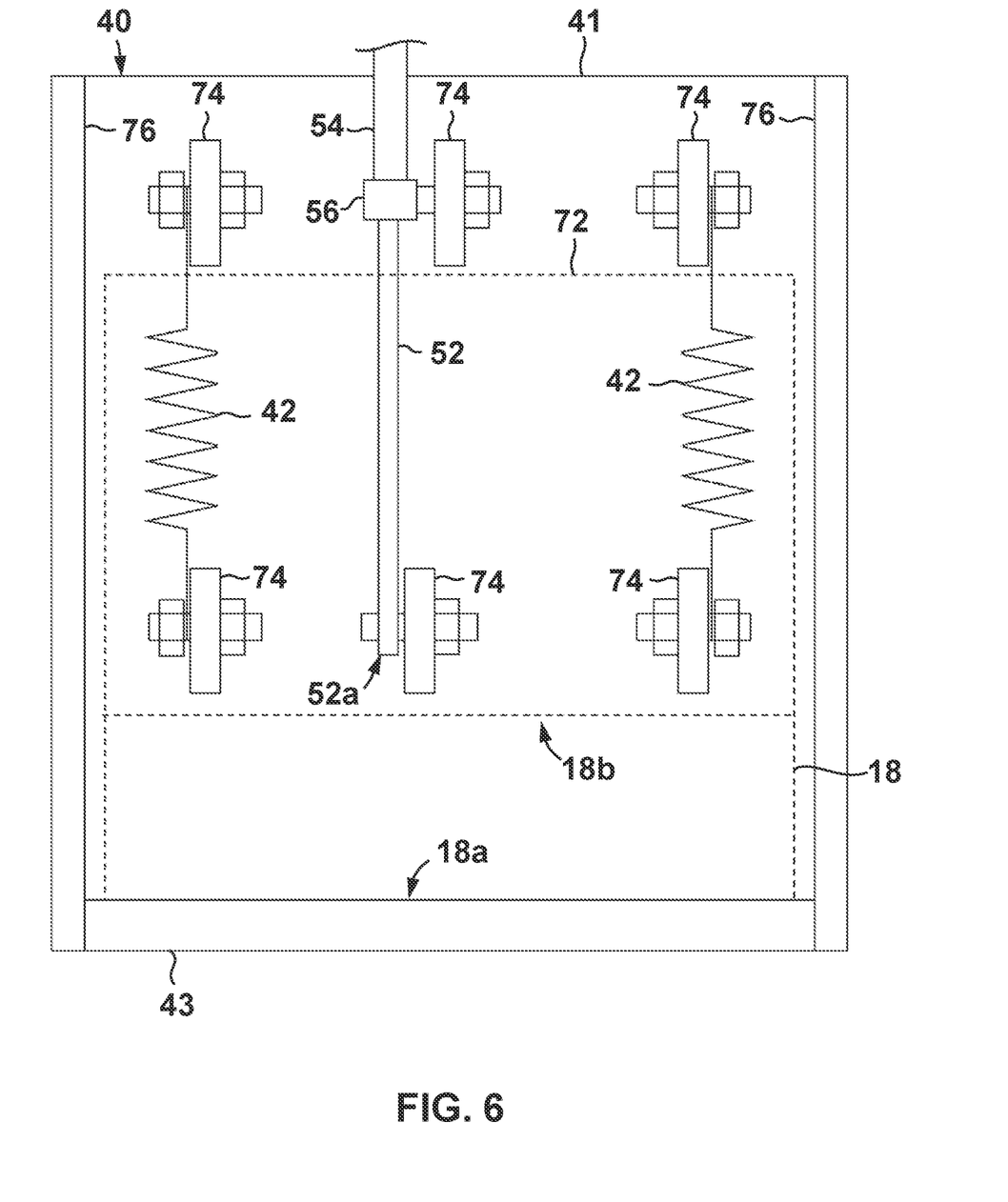

Referring now to FIGS. 5 and 6, in some embodiments, support frame 40 may include a pair of side walls 76 coupled to the vertical portion 41 and lateral portion 43 (not shown in FIG. 5, but shown in FIGS. 3 and 4). In addition, in some embodiments, a pedal 18 may comprise a back wall 72 coupled to and extending (e.g., extending normally) from second end 18b. Referring briefly not to FIGS. 1, 5, and 6, when support frame 40 and pedal 18 are installed within second recess 16 of outer housing 12, the side walls 76 and back wall 72 may occlude the other components (e.g., cable 52, biasing member(s) 42, etc. coupled within and to support frame 40 so as to protect them from damage during operations.

Referring again to FIGS. 5 and 6, in some embodiments, a pair of biasing members 42 are engaged to bracket members 74 coupled to both vertical portion 41 of support frame 40 and back wall 72 of pedal 18 (note: pedal 18 is shown in broken line in FIG. 6 so as to better illustrate the other components depicted in the drawing). In addition, the first end 52a of cable 52 may be coupled to a bracket 74 coupled to back wall 72 of pedal 18, while protective sheath 54 may be coupled to the pivoting cable restraint 56 mounted to another bracket 74 in vertical portion 41 of support frame 40. During operations, the biasing members 42 may rotationally bias second end 18b of pedal 18 upward and away from lateral portion 43 (FIGS. 3 and 4) about first end 18a as previously described, and movement of the pedal 18 may cause sliding engagement of the first end 52a of cable 52 into and out of sheath 54 as previously described.

Figure 7:
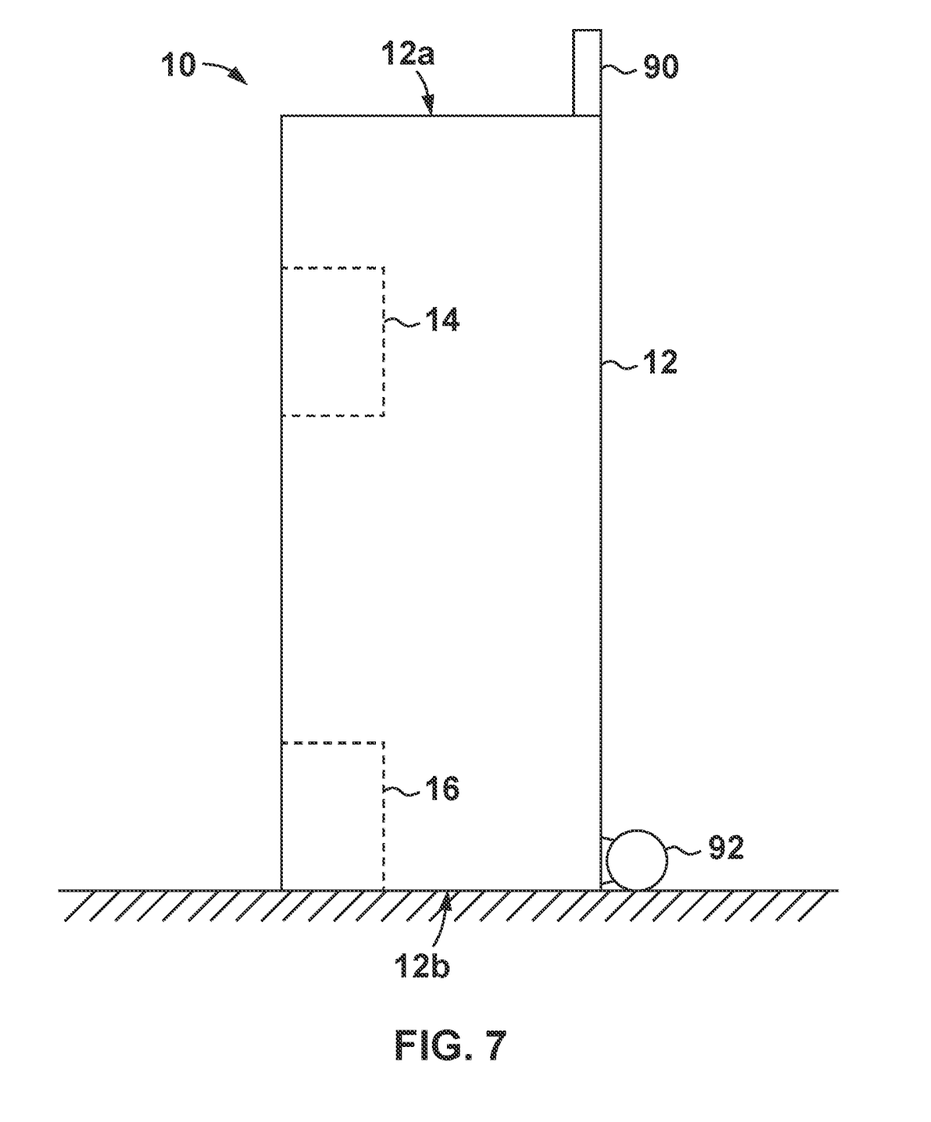
FIG. 7 is a side view of a hand sanitizing station according to some embodiments.

Referring now to FIG. 7, in some embodiments, outer housing 12 of hand sanitizing station 10 may comprise a handle 90 at or proximate upper end 12a. In addition, the outer housing 12 may comprise one or more wheels 92 at or proximate to bottom end 12b. During operations, the outer housing 12 may be tipped or leaned so as to rest on wheel(s) 92). Thereafter, while maintain the tipped or angled position of the outer housing 12, one may push or pull on the handle 90 to roll the outer housing 12 to a desired position. In some embodiments, lower end 12b of housing 12 may include one or more recesses (not shown) so that the housing 12 may be lifted with the lifting arms of a forklift or similar device.

Referring again to FIGS. 1-3, in some embodiments, outer housing may include additional sanitation or hand washing stations. For instance, in some embodiments, multiple (e.g., a plurality of) flow control valve assemblies 30 (FIG. 3) may be positioned along outer housing 12 (e.g., via recesses 14), each flow control valve assembly 30 being actuatable to dispense hand sanitizer 15 via a corresponding pedal 18 associated therewith. In some embodiments, multiple hand sanitization stations 10 may be engaged with one another (e.g., side-by-side, back-to-back, etc.) to define multiple hand sanitizing stations 10 within a defined area.

Figure 8:
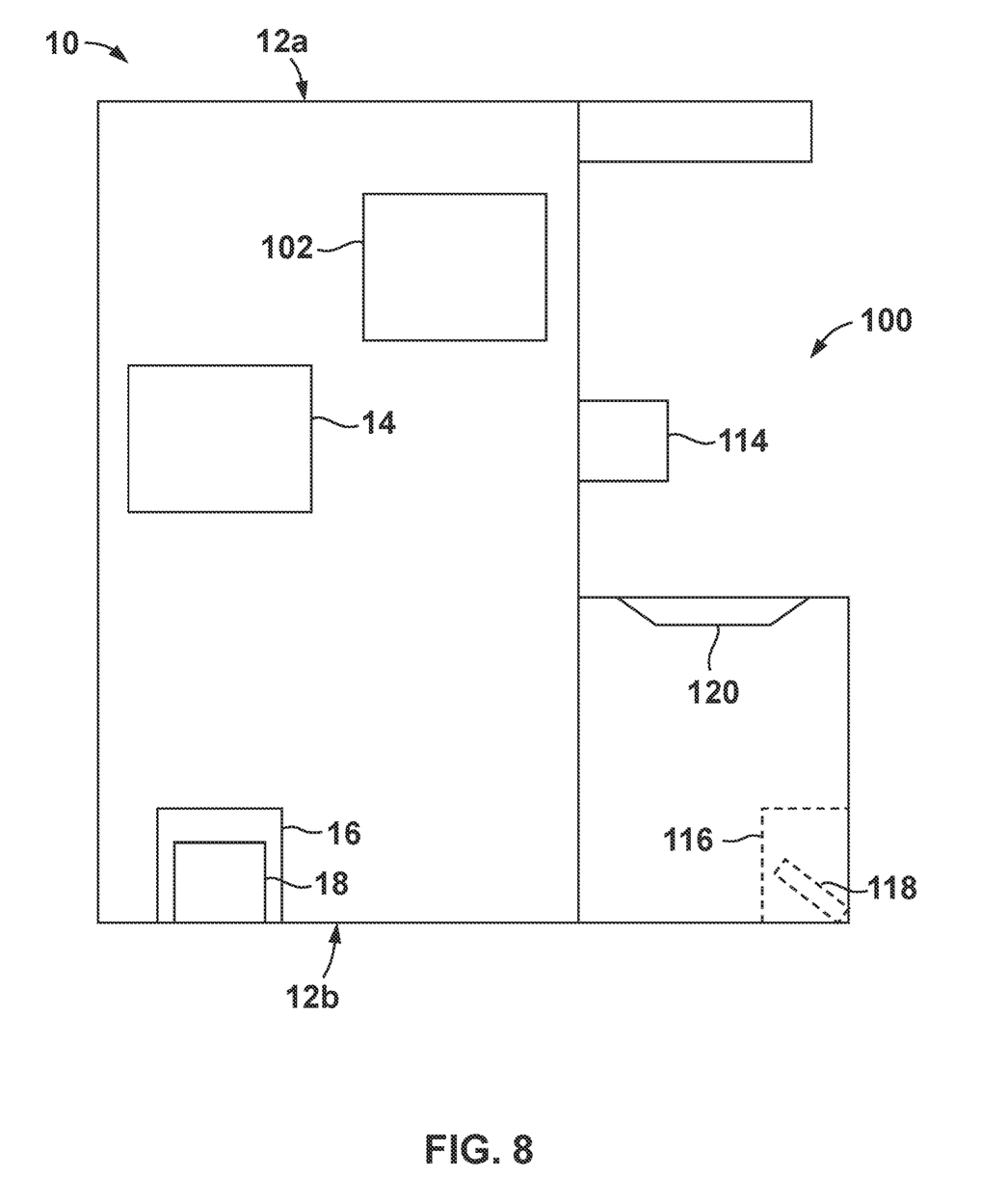
FIG. 8 is a is a front view of a hand sanitizing station according to some embodiments.

Referring now to FIG. 8, in some embodiments, the outer housing 12 may also include a hand washing station 100 in addition to the hand sanitizer dispensing components previously described above. For instance, the hand washing station 100 may comprise one or more dispensers 114 for dispensing water and/or soap. Each dispenser 114 may dispense the water or soap via actuation of a corresponding pedal 118. In some embodiments, separate supply tanks (e.g., supply tank 20) may be positioned within outer housing 12 that hold volumes of water and/or soap for dispensing from dispensers 114. The actuation of pedal 118 may cause a metered amount of water and/or soap to be dispensed from dispensers 114 in substantially the same manner as previously described above for hand sanitizer from nozzle 32. Thus, in some embodiments, additional flow control valve assemblies 30 and mechanism coupling assemblies 50 may be coupled to pedal 118 in the same manner as described above for pedal 18 so that user's actuation of the pedal 118 (e.g., via a foot) may cause water and/or soap to be dispensed from dispensers 114 in substantially the same manner as described herein. Thus, in some embodiments, the dispensing system for dispensing water and/or soap from the dispensers 114 may be independent of the system described herein for dispensing hand sanitizer from nozzle 32.

In addition, a basin 120 may be positioned below dispensers 114 that may catch waste water and/or soap and fluidly communicate the waste water and/or soap to a waster tank (e.g., the waste tank 38 shown in FIG. 2 and/or a separate waste tank within outer housing 12). Further, in some embodiments, additional dispensers 102 may be included on housing 12 that may be configured to dispense paper towels or napkins.

AS described above, the embodiments disclosed herein include a self-contained hand sanitation station that operates without electricity or other sources of power and relies instead on the head pressure of the sanitizer that is retained in a reservoir. A measured amount of fluid sanitizer is metered out of the apparatus onto the patron's hands as controlled by a foot pedal that the patron depresses. Accordingly, through use of the embodiments disclosed herein, patrons to an establishment or venue may more easily engage in hand sanitization.

While exemplary embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A hand sanitizing station, comprising:
   a conduit in fluid communication with a source of sanitizer, the conduit having a fluid outlet;
   a valve coupled to the conduit and configured to control the volume of sanitizer that exits the fluid outlet, the valve having a control arm;
   a pedal;
   a cable connected between the pedal and the control arm of the valve, wherein the pedal is configured to apply a tension to the cable to move the control arm in response to depression of the pedal whereby the valve is opened a predetermined amount;
   wherein movement of the pedal from a first position to a second position causes sanitizer to flow by gravity from the conduit and out of the fluid outlet; and
   wherein movement of the pedal from the second position back to the first position closes the valve.

2. The hand sanitizing station of claim 1 wherein sanitizer is dispensed by head pressure alone.

3. The hand sanitizing station of claim 1 where the hand sanitizing station is pumpless.

4. The hand sanitizing station of claim 1 further comprising:
   a supply tank of sanitizer and a housing; and
   wherein the reservoir, the valve, the conduit, fluid outlet, the cable and the foot pedal are all housed in the housing.

5. The hand sanitizing station of claim 4 wherein the housing has a first recess beneath the fluid outlet and configured to allow a user to insert the user's hands beneath the fluid outlet, and a second recess configured to allow a user to depress the foot pedal with a foot.

6. The hand sanitizing station of claim 1 further comprising a stop configured to limit the travel of the pedal and to meter the amount of sanitizer passing though the valve.

7. The hand sanitizing station of claim 1 wherein the valve is a ball valve.

8. The hand sanitizing station of claim 1, wherein the valve is a barrel valve.

9. The hand sanitizing station of claim 1 further comprising a water dispensing system that is independent from the source of sanitizer.

10. The hand sanitizing station of claim 1 that is free of a power source.

11. A method of sanitizing hands, comprising:
   (a) depressing a pedal on a hand sanitizing station;
   (b) applying a tension to a cable connected between the pedal and a control arm of a valve positioned within a housing of the hand sanitizing station as a result of (a);
   (c) actuating the valve as a result of (b); and
   (d) flowing sanitizer from a supply tank positioned within the hand sanitizing station through a nozzle as a result of (b) under the force of gravity.

12. The method of claim 11, wherein (b) comprises actuating the valve proportionally to a depression of the pedal during (a).

13. The method of claim 11, wherein (b) comprises pulling a cable that is coupled to the pedal and a control arm of the valve.

14. The method of claim 11, wherein the valve is a ball valve.

15. The method of claim 11, wherein the valve is a barrel valve.

16. The method of claim 11, further comprising:
(e) releasing the pedal after (b); and
(f) rotating the pedal via a biasing member after (e).

* * * * *